United States Patent
Rantala

[11] Patent Number: 5,091,649
[45] Date of Patent: Feb. 25, 1992

[54] REMOVAL OF GASES DISTURBING THE MEASUREMENTS OF A GAS DETECTOR

[75] Inventor: Börje T. Rantala, Helsinki, Finland

[73] Assignee: Instrumentarium Corporation, Finland

[21] Appl. No.: 549,562

[22] Filed: Jul. 6, 1990

[30] Foreign Application Priority Data

Jul. 7, 1989 [FI] Finland .................. 893329

[51] Int. Cl.⁵ .............................................. G01N 21/35
[52] U.S. Cl. ....................................... 250/343; 250/339
[58] Field of Search .............. 250/343, 344, 345, 346, 250/339; 356/437, 438, 439

[56] References Cited

U.S. PATENT DOCUMENTS

| | | | |
|---|---|---|---|
| 4,567,366 | 1/1986 | Shinohara | 250/339 |
| 4,577,105 | 3/1986 | Krempl et al. | 250/343 |
| 4,793,830 | 12/1988 | Murphy et al. | |
| 4,803,370 | 2/1989 | Eckles | 250/504 R |
| 4,914,719 | 4/1990 | Conlon et al. | 250/339 |

Primary Examiner—Constantine Hannaher
Assistant Examiner—Edward J. Glick
Attorney, Agent, or Firm—Andrus, Sceales, Starke et al.

[57] ABSTRACT

The invention relates to a gas detector for measuring one or more hydrocarbons or some other gas having its infrared absorption spectrum partially or entirely overlapping with water and, in addition, carbon dioxide and/or nitrogen oxide. The gas detector comprises a radiation source (1), a measuring chamber (3), a reference chamber (4), the electromagnetic radiation coming from the radiation source passing through said chambers, and a radiation detector (5). A beam passing from radiation source (1) both to measuring chamber (3) and to reference chamber (4) and from these chambers further to detector (5) travels in a space (14) which is provided with both a carbon-dioxide removing material (11) and a water-removing material (12). The invention relates also to a method for absorbing the carbon dioxide contained in said gas detector space (14) or in a part of this space into a carbon-dioxide removing material (11) and for absorbing the water into a water-removing material (12).

17 Claims, 1 Drawing Sheet

REMOVAL OF GASES DISTURBING THE MEASUREMENTS OF A GAS DETECTOR

BACKGROUND OF THE INVENTION—FIELD OF THE INVENTION

The present invention relates to a gas detector for measuring one or more hydrocarbons or some other gas having its infrared absorption spectrum partially or entirely overlapped with water and, in addition, carbon dioxide and/or nitrogen oxide, and to a method for removing the measurement-disturbing gases contained in a gas detector from that space or a part of that space remaining outside the measuring chamber, in which the electromagnetic radiation emitted from a radiation source travels to a radiation detector.

BACKGROUND OF THE INVENTION—DESCRIPTION OF THE RELATED ART

In present gas detectors for measuring carbon dioxide and nitrogen oxide concentrations, the measurement-disturbing carbon dioxide contained in the detector is removed by means of an absorber which consists of hydroxides of alkali metals. As a result, this carbondioxide removing reaction produces e.g. water. In the measurements of carbon dioxide and nitrogen oxide this resulting water does not cause problems.

The separate measurements of the concentrations of hydrocarbons, such as e.g. anesthetic gases, have not required absorbers since indoor air does not contain hydrocarbons in disturbing concentrations and, in addition, it has been possible to ventilate the entire detector, and especially the reference chamber, into open air.

When a detector measuring carbon dioxide and nitrogen oxide concentrations is combined with a detector measuring hydrocarbons, e.g. anesthetic gases, there are problems caused by disturbing compounds which are found in the measuring space and which absorb electromagnetic radiation, such as e.g. infrared radiation, leading to incorrect measuring results. Particularly in the measurement of hydrocarbons, the source of problems is water which is thus produced when measuring the concentrations of carbon dioxide and nitrogen oxide. Water causes intensive absorption within that very infrared range in which the measuring of hydrocarbons is indeed effected. In such a closed system, the measuring of hydrocarbons is also disturbed by hydrocarbons released from the gluings of a detector or the motor oils of an optical chopper.

SUMMARY OF THE INVENTION

An object of this invention is to eliminate the above problems. An object of the invention is to provide a common measuring unit both for a gas, such as hydrocarbon, having its infrared absorption spectrum partially or entirely overlapping with water and for carbon dioxide and/or nitrogen oxide, whereby the operation of such unit is not disturbed by water. An object of the invention is also to provide a common measuring unit both for a gas, such as hydrocarbon, having its infrared absorption spectrum partially or entirely overlapping with water and for carbon dioxide and/or nitrogen oxide, whereby the operation of such unit is not disrurbed by hydrocarbon outside the measuring chamber.

The characterizing features of a disturbing-gases absorbing gas detector of the invention and those of a related method are set forth in the annexed claims.

The invention is based on using a common gas detector for measuring both one or more hydrocarbons or some other gas having its infrared absorption spectrum partially or entirely overlapping with water and carbon dioxide and/or nitrogen oxide, wherein the carbon dioxide, and particularly the water produced in connection with the removal of carbon dioxide, disturbing the electromagnetic radiation arriving in a gas detector are removed by means of a material absorbing such compounds. A suitable water-absorbing material is e.g. silica gel or even calcium sulphate. Other water-absorbing chemical compounds are also known. In addition to carbon dioxide and water disturbing the electromagnetic radiation arriving in a gas detector, also the hydrocarbon is preferably removed by means of a material absorbing it. A suitable material for absorbing hydrocarbons is preferably activated carbon or some activatedcarbon based material. Also other hydrocarbons-absorbing materials can be employed.

BRIEF DESCRIPTION OF THE DRAWING

The invention will now be described in more detail with reference made to the accompanying drawing, in which.

DESCRIPTION OF THE PREFERRED EMBODIMENT

Figure 1:
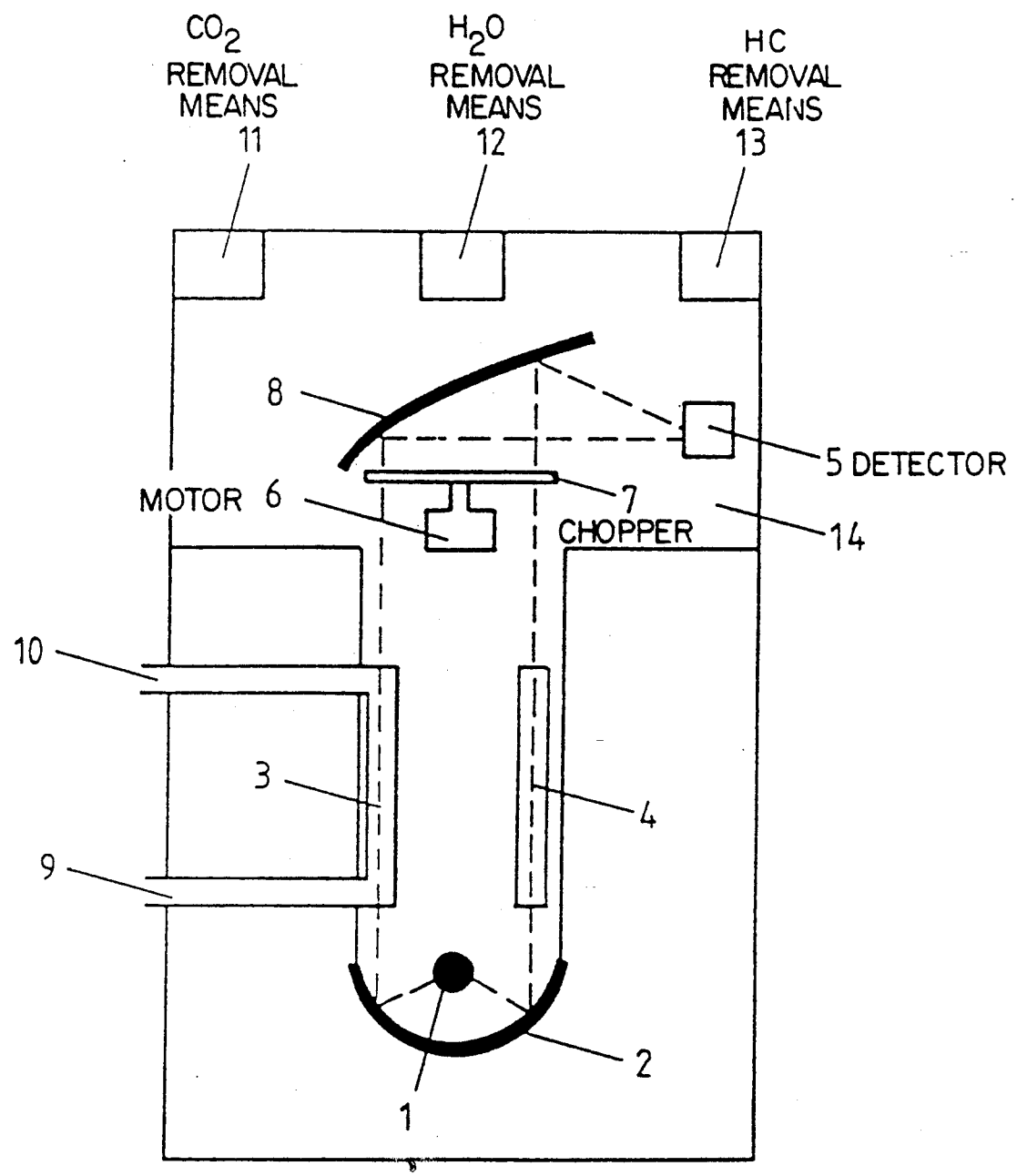
FIG. 1 illustrates a gas detector for examing hydrocarbons, carbon dioxide and nitrogen oxide, said gas detector including, in addition to a carbon-dioxide absorbing material, materials of the invention absorbing water and hydrocarbons.

A gas detector shown in FIG. 1 is mostly of a conventional structure, i.e. the radiation coming from a radiation source 1 is reflected by a mirror 2 through a measuring chamber 3 and a reference chamber 4 to a radiation detector 5. A radiation chopper 7, preferably a rotating disc, is driven by a motor 6 to guide the beams, which are passing alternately through the measuring chamber and the reference chamber, by way of a mirror 8 to the detector. Gas arrives in the measuring chamber along a tube 9 and escapes therefrom along a tube 10. According to the invention, in addition to a carbondioxide removing material 11, the gas detector is also provided with a water-removing material 12 produced as a result of the mainly carbon-dioxide removing reaction. Furthermore, the gas detector preferably contains one or more hydrocarbon-removing materials 13. Such materials 11, 12 and 13 removing measurements-disturbing gases are contained in a space 14, which is preferably hermetically sealed. Said space 14 comprises a passage leading both from radiation source 1 to measuring chamber 3 and from the measuring chamber to detector 5 as well as from radiation source 1 by way of reference chamber 4 to detector 5, the beams emitted from radiation source 1 advancing through this passage. Thus, the closed space 14 is not in communication with measuring chamber 3. Neither is it required that reference chamber 4 be in communication with closed space 14 although, in the most preferred case, it is indeed in communication therewith.

According to the invention, when using expellers of measurements-disturbing gases, the identifications and concentration measurements of carbon dioxide, nitrogen oxide either a hydrocarbon, such as anesthetic gas, or a gas having its infrared absorption spectrum partially or entirely overlapping with water can be reliably performed in one and same detector. Conventional anesthetic gases considered as hydrocarbons include isoflurane, enflurane, methoxyflurane and halothane.

The invention is by no means limited to the embodiment shown in the figure but various details of the invention can be modified within the scope of the annexed claims.

I claim:

1. A gas detector for measuring both an anesthetic gas, the infrared absorption spectrum of which is partially or entirely overlapping with that of water, and at least one of carbon dioxide and an oxide of nitrogen, said detector comprising:
    a measuring chamber (2) through which the gas to be measured flows;
    a reference gas chamber (4);
    an infrared radiation source, the infrared radiation of which passes through said measuring and reference chambers;
    a radiation detector (5) for receiving the radiation after passage through said measuring and reference chambers; and
    housing means defining a space (14) containing said measuring chamber, reference chamber, radiation source and radiation detector and through which the radiation passes to said chambers and from said chambers to said radiation detector, said housing containing, in said space, means (11) for removing carbon dioxide from said space and means (12) for removing water from said space.

2. A gas detector as set forth in claim 1 wherein said housing further contains, in said space, means (13) for removing hydrocarbons from said space.

3. A gas detector as set forth in claim 2, characterized in that said hydrocarbon-removing means (13) contains activated carbon.

4. A gas detector as set forth in claim 1, characterized in that said carbon-dioxide removing means (11) contains alkali metal hydroxide.

5. A gas detector as set forth in claim 1, characterized in that said water-removing means (12) contains silica gel.

6. A gas detector as set forth in claim 1, characterized in that said water-removing means (12) contains calcium sulphate.

7. A gas detector as set forth in claim 1, characterized in that said housing means is hermetically sealed.

8. A gas detector as set forth in claim 1 characterized in that said reference chamber (4) is in communication with said space defined by said housing means 9. A method for measuring both an anesthetic gas, the infrared absorption spectrum of which is partially or entirely overlapping with that of water, and at least one of carbon dioxide and an oxide of nitrogen, said method comprising the steps of:
    flowing the gas to be measured through a measuring chamber;
    passing infrared radiation through the measuring chamber and through a reference gas chamber;
    detecting the radiation after passage through said measuring and reference chambers with a radiation detector; and
    removing carbon dioxide and water from the path of the infrared radiation to said chambers and from said chambers to said radiation detector.

10. A method as set forth in claim 9 further defined as including the step of removing hydrocarbons from the path of the infrared radiation to said chambers and from said chambers to said radiation detector.

11. A method as set forth in claim 10 further defined as removing the hydrocarbon by absorbing same into an activated carbon.

12. A method as set forth in claim 9 further defined as removing the carbon dioxide by absorbing same into an alkali-metal hydroxide.

13. A method as set forth in claim 9 further defined as removing the water by absorbing same into a silica-gel.

14. A method as set forth in claim 9 characterized as removing the water by absorbing same into a calcium-sulfate.

15. A method as set forth in claim 9 further defined as removing the carbon dioxide and water from a hermetically sealed spaced containing the path of the infrared radiation.

16. A method as set forth in claim 9 further defined as removing the water and carbon dioxide from the reference chamber.

17. A method as set forth in claim 9 further defined as passing the radiation through a reference chamber that is not in communication with a space containing the path of the infrared radiation.

* * * * *